United States Patent [19]

Hunt et al.

[11] Patent Number: 4,683,035
[45] Date of Patent: Jul. 28, 1987

[54] METHOD FOR IN SITU CORROSION DETECTION USING ELECTROCHEMICALLY ACTIVE COMPOUNDS

[75] Inventors: Barry E. Hunt, Aurora; Harvey M. Herro, Naperville, both of Ill.; Kyu-Hwa Lee, Kyungnam, Rep. of Korea; Morris Mindick, Downers Grove, Ill.

[73] Assignee: Nalco Chemical Company, Oak Brook, Ill.

[21] Appl. No.: 825,703

[22] Filed: Feb. 3, 1986

[51] Int. Cl.$^4$ .......................................... G01N 27/46
[52] U.S. Cl. .................................. 204/1 T; 204/404; 436/6; 436/34; 436/164; 436/904
[58] Field of Search ................... 204/1 C, 404; 436/6, 436/34, 164, 904

[56] References Cited

U.S. PATENT DOCUMENTS 2,963,349 12/1960 Bernard et al. ........................ 436/6
3,079,343 2/1963 Bernard ................................. 436/6

FOREIGN PATENT DOCUMENTS 934323 6/1982 U.S.S.R. ............................ 436/164

Primary Examiner—T. Tung
Attorney, Agent, or Firm—John G. Premo; Anthony L. Cupoli; Donald G. Epple

[57] ABSTRACT

The invention comprises a method for determining the corrosion rate of metals in contact with a liquid system which is capable of causing corrosion of such metals which comprises adding to the liquid system an electrochemically active compound having a reduction potential more positive than the metal in contact with the liquid system and then monitoring the system thus treated with the electrochemically active compound to determine its rate of reduction which is proportional to the corrosion rate of the metal.

3 Claims, 2 Drawing Figures (ISU DIAGRAM)

(ISU DIAGRAM)

METHOD FOR IN SITU CORROSION DETECTION USING ELECTROCHEMICALLY ACTIVE COMPOUNDS

BACKGROUND OF THE INVENTION

1. Field of the Invention

This invention relates to a corrosion detection method. More particularly, it is concerned with a corrosion detection agent which uses a water-soluble, electrochemically active compound to measure metal corrosion rates. The degree of reduction of the electrochemically active agent is correlated with the corrosion rate.

2. Description of the Prior Art

A major concern of chemical treatment in water systems is determination of the system metal corrosion rates. Without corrosion rate data, product overfeeding or underfeeding is common, which often is expensive or ineffective, and can lead to other problems.

Presently, corrosion can be detected either directly or indirectly. Direct detection is done by weight loss of the metal part itself (used in laboratory studies, but impractical in a plant situation), by visual inspection (expensive, time-consuming, and sometimes impossible), or by a variety of instrumental techniques (radiography, ultrasonics, eddy-current, thermography, acoustic emission) which are expensive and awkward or impossible in situ.

Indirect detection (metal coupons, corrosion meters) measures the corrosion potential of the water but does not tell whether active corrosion of plant equipment is occurring.

None of the presently used methods is able to give accurate corrosion rate measurements in a plant environment. Nevertheless, such techniques continue to be used because the resulting information is better than no information.

While the principle of using organic compounds to detect reducing sites in bacteria is widely used, no example has been found in the technical literature for using organic compounds for detecting reducing metal sites, e.g. corrosion.

SUMMARY OF THE INVENTION

This invention provides a technique for "in situ" detection of corrosion in a liquid system at a metal surface using an electrochemically active compound added to the system. When corrosion occurs, the compound is reduced by the electrons released at the cathodic site. The reduced form of the compound is then measured by analytical techniques. The amount of the reduced form of the compound is correlated with the amount of active corrosion.

DEFINITIONS

"In situ" means that the active compound is reduced at the site where the electrons are being released.

"Corrosion" means that the metal is undergoing any process which releases electrons which then react with the active agent. This definition includes simple corrosion (iron going to ferrous ions or compounds, copper going to cuprous ions or compounds) or change of oxidation state (ferrous ions or compounds going to ferric ions or compounds).

"Metal surface" applies to any surface which releases electrons, such as iron, steel, cast iron, brass, aluminum, other non-ferrous alloys, or to the oxide, other metal compounds, and/or other corrosion products overlaying the metal surface.

"Liquid system" means that the concept is not limited to water systems; the concept applies to any liquid system (including aqueous, non-aqueous, and mixed) in which electrons are released during corrosion and the active agent is carried to the site to receive the electrons.

"Aqueous systems" include cooling towers, boilers, condensers, heat exchangers, and closed cooling systems.

"Non-aqueous" systems include solvent-based or petroleum oil type systems. Mixed systems include oil-brine mixtures found in injection wells.

"Electrochemically active compound" means any substance which has the proper reduction potential to receive electrons at the active site. Included would be redox type indicators (I) and organic compounds in general (II). While it can be seen that a wide variety of materials may be suitable for this technique, in general, the detecting substance should have the following characteristics:

(1) have the proper reduction potential;
(2) be soluble in the system (or, at least, be capable of being carried to the active site);
(3) be reduced irreversibly (or the re-oxidation reaction should be kinetically slow);
(4) the reduced form is analytically detectable.

THE INVENTION

Figure 1:
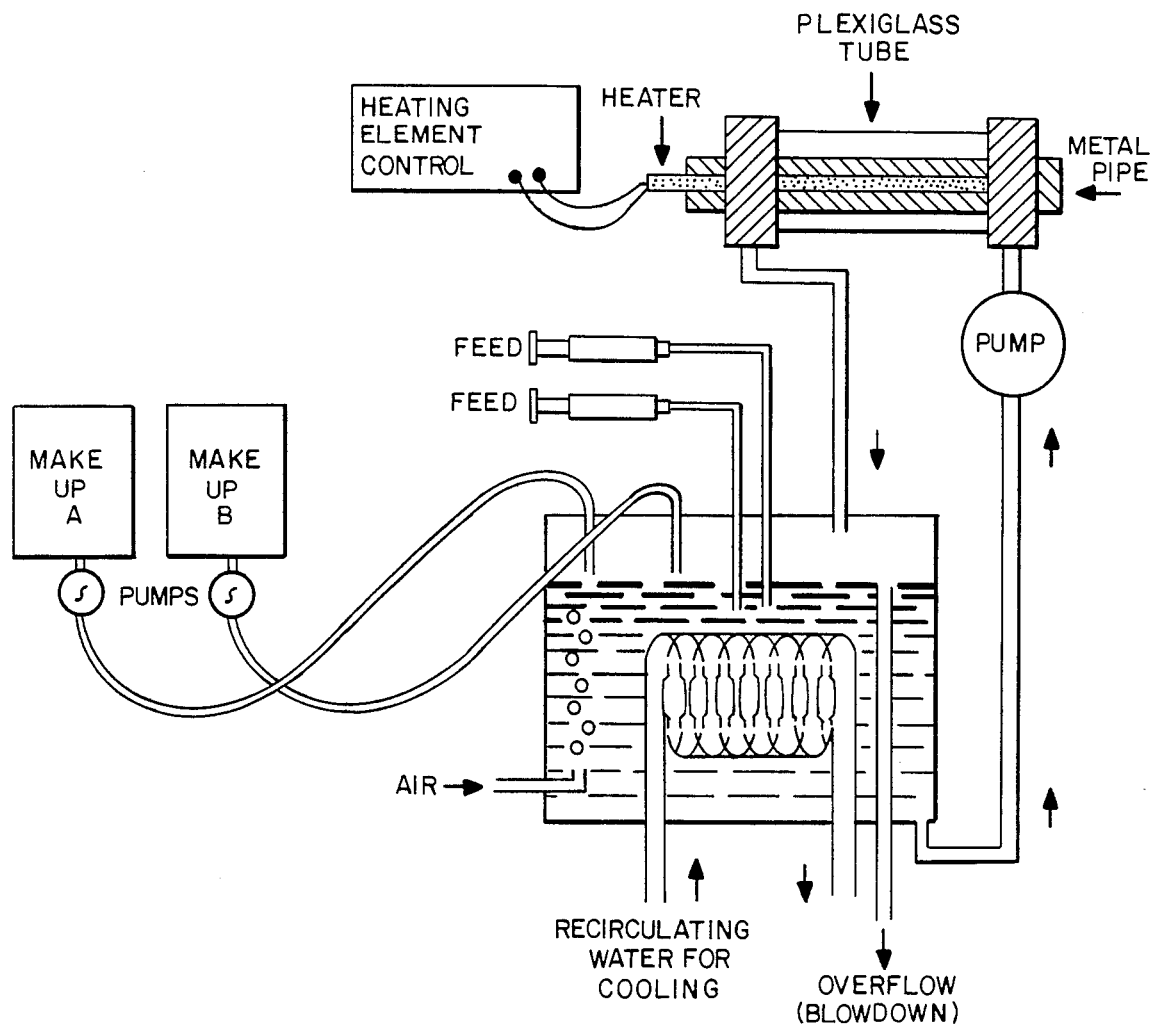
FIG. 1 is a diagramatic view of a pilot cooling tower apparatus.

The invention comprises a method for determining the corrosion rate of metals in contact with a liquid system. An electrochemically active compound having a reduction potential more positive than the system metal surface potential is added to the liquid system. The system is monitored to determine the active compound reduction rate. The reduction rate is related to the corrosion rate of the metal.

Some of the aforementioned electrochemically active agents are novel water-soluble tetrazolium compounds having the formula:

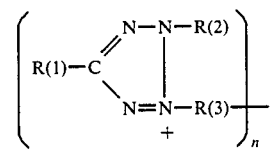

In the above formula, $R_1$, $R_2$, and $R_3$ are from the group consisting of lower alkyl, aryl, aralkyl, heterocyclic substituted aryl with the proviso that neither $R_1$, $R_2$, or $R_3$ contain more than 14 carbon atoms and n may be 1 or 2.

Specific examples of preferred compounds are
2-(p-carboxyphenyl)-3,5-diphenyl-tetrazolium salt,
3-(p-carboxyphenyl)-2,5-diphenyl-tetrazolium salt,
2-(o-carboxyphenyl)-3,5-diphenyl-tetrazolium salt, and
3-(o-carboxyphenyl)-2,5-diphenyl-tetrazolium salt.

SPECIFICS OF THE INVENTION

The reduction potential of the corroding surface will determine the choice of the electrochemically active compound to be used. Tables of reduction potentials of metals under a variety of conditions are available to help make that choice. See *Atlas of Electrochemical Equilibria in Aqueous Solutions,*" by Marcel Pourbaix, Pergamon Press (1966) Oxford, Cebelcor, Brussels.

The electrochemically active compound should have a reduction potential more positive than the system corrosion reaction for the reaction to be thermodynamically possible. Tables of reduction potentials of electrochemically active compounds are available to help in choosing. See *CRC Handbook Series in Organic Electrochemistry,* Louis Meites and Petr Zuman, CRC Press, Inc. (1977) Cleveland. Reduction potentials can also be determined experimentally using well known instrumental techniques such as polarography and cyclic voltammetry. However, it is well known that environmental factors at the corrosion site can radically alter the predicted reduction potential. In addition, while a reaction may be thermodynamically possible, it may not be kinetically favored. Thus, empirical testing will frequently be needed to find the proper electrochemically active agent for a particular system.

Examples of redox indicators of the general class (I) are neutral red, resazurin, methylene blue, eriochrome black T, bromocresol purple, phenol red, methyl viologen, alizarin red S, and fluoroscein.

Examples of organic compounds in general class (II) are o-dinitrobenzene, m-dinitrobenzene, p-dinitrobenzene, 2,5-dinitrophenol, 3,4-dinitrobenzoic acid, 3,4-dinitrobenzyl alcohol, 3,5-dinitrobenzoic acid, 2,3,5-triphenyltetrazolium chloride, 2-(p-carboxyphenyl)-3,5-diphenyltetrazolium bromide,
2-(o-carboxyphenyl)-3,5-diphenyltetrazolium bromide,
3-(p-carboxyphenyl)-2,5-diphenyltetrazolium bromide,
3-(o-carboxyphenyl)-2,5-diphenyltetrazolium bromide, Tetrazolium Blue
[3,3'-(3,3'-dimethoxy-(1,1'-biphenyl)-4,4'-diyl)-bis(2,5-diphenyl-2H-tetrazolium)dichloride], Tetrazolium Violet
[2,5-diphenyl-3-(alpha-naphthyl)tetrazolium chloride], MTT
[3-(4,5-dimethylthiazol-2-yl)-2,5-diphenyltetrazolium bromide],
Neotetrazolium chloride [2,2',5,5'-tetraphenyl-3,3'(p-diphenylene) ditetrazolium chloride], Nitro Blue Tetrazolium
[2,2'-di-n-nitrophenyl-5,5'-diphenyl-3,3'(3,3'-dimethoxy-4,4'-diphenylene)ditetrazolium chloride, Tetra Nitro Blue Tetrazolium
[2,2',5,5'-tetra-p-nitrophenyl-3,3'-(3,3'-dimethoxy-4,4'diphenylene)ditetrazolium chloride], Thiocarbamyl Nitro Blue Tetrazolium
[2,2'-di(p-nitrophenyl)-5,5'-di(p-thiocarbamylphenyl)-3,3'-(3,3'-dimethoxy-4,4'-biphenylene)ditetrazolium chloride], Iodo Nitro Tetrazolium Violet
[2-(4-iodophenyl)-3-(4-nitrophenyl)-5-phenyl-tetrazolium chloride], 3-cyanopyridine, 4-cyanopyridine,
2-chloro-2-nitrosopropane, 4-aminoazobenzene,
2-bromo-2-nitropropane, 2-bromo-2-nitroso-propane,
p-phenylenediamine, 3-diazo-1,3-dihydro-2H-indol-2-one,
-methylhydroxylamine, 1-isonicotinoyl-2-phenylhydrazine,
1-nitroso-2-naphthol, diphenyliodonium p-toluenesulfonate,
2-nitroso-1-naphthol-4-sulfonic acid, 2-chloro-2-nitropropane,
1,4-benzoquinone, 2-nitroso-1-naphthol, nitrosobenzene,
2-(4'-hydroxyphenylazo)pyridine, 1,4-napthoquinone,
6-methoxy-1-hydroxyphenazine-5,10-dioxide, formaldoximeazocarbamide, 1-nitrosoacetaldoxime,
1,4-dinitrobenzene, 1,4-dinitronaphthalene, azobenzene,
1,2-dinitrobenzene, azobis(formaldoxime), benzonitrile oxide,
2,2-dinitropropane, 4-(phenylazo)azobenzene, 4-nitrosophenol,
2-nitrofuran, 1,3-dinitrobenzene, 2,2'-pyridil, nitrobenzene,
dimethylphenacylphenylammonium bromide, 1,1-dinitroethane,
bis-4-pyridoxyldisulfide, 2-ninhydrin monoxime,
6-hydroxypteridine, phenylglyoxal aldoxime, phenylglyoxal
2-hydrazone, 3-nitrophenol, azooxybenzene, 4-nitroaniline,
w-diazoacetophenone, 1-methyl-4-cyanopyridinium iodide, methyl vinyl ketone, 1-(4-methoxyphenyl)-3-(2-quinolyl)-2-propen-1-one,
6-methylpterin, diethyl bromomaleate, 2-nitrophenol,
diethylphenacylsulfonium bromide, 2-methyl-2-nitratopropanoic acid, 7-hydroxypteridine, 3-diazocamphor, 4-nitrophenol, isatin 3-(O-ethyloxime), N-nitropiperidine, 1,2-ninhydrin dioxime, 1,3-ninhydrin dioxime, diethyl bromofumarate, 2-iodopyridine, syn-phenyl 2-pyridyl ketone oxime, pyridazine, triphenylsulfonium chloride, phenacylpyridinium chloride,
1,2-diisonicotinoylhydrazine, N-nitroaniline, cinnamaldehyde,
1,2-indandione-2-oxime, 4-iodopyridine, 4-cyanopyridine,
3-iodopyridine, 2,4-hexadienal, purine-6-sulfonic acid, N-nitrosopiperidine, chloromaleic acid, benzaldehyde,
phenylethylhydrazine, 2,3-dihydro-(3-oxo)thianaphthene, maleic acid, 2-methyl-2-phenoxypropanal, ethyl pyruvate semicarbazone, bromofumaric acid, chalcone, 4-cyanocinnamic acid, 4-cyanophenyl methyl sulfone, bromomaleic acid, glycolaldehyde,
2-methyl-2-nitratopropanol, 2-(methylthio)-2-methylpropanal, dipropyl N-nitrosoamine, 1,2-bis(2-thenoyl)ethane,
3-phenylpropanal, ethyl methacrylate, 4-cyanobenzoic acid,
4-methylsulfonylbenzoic acid, isobutyraldehyde, 3-cyanobenzoic acid, 2-cyanopyridine, 3-cyanopyridine, catechol, resorcinol, and phenylhydroxylamine. Among these compounds, the tetrazolium compounds are preferred for ease of analysis in a water-based system.

Dosage

The dosage of the compound will depend upon such variables as the liquid system into which it is employed, the metal which is oxidized to react with the compound, its rate of reaction, and the stability of the reduced form. Further considerations are its susceptibility to a particular analytical technique employed to determine its presence in its reduced form. In certain cases the amount can be as low as a few ppb (parts per billion) although as a general rule the dosage will be between about 0.01 up to no more than 100 ppm. Typically dosages within the range of 0.05-10 ppm allow adequate determination of the corrosion occurring in the system to be measured.

Analytical Methods

As indicated, a variety of analytical techniques may be used to determine the degree of reduction of the electrochemically active compound. The techniques used will depend on such factors as the characteristics of the reduced form of the electrochemically active compound, the amount and kind of interferences, the degree of corrosion being measured and the volume of the system in which it is occurring, the sensitivity and accuracy required, the degree of expertise of the analyst, the funds available for the analysis program, and whether the analyses are needed continuously or occasionally.

In some cases, concentration techniques such as liquid-liquid extraction and adsorption onto a solid phase will be needed to allow the use of the desired analytical procedure.

In the case where the reduced form is colored, color comparison charts, color comparitors, or simple colorimeters may be all that is required for analysis.

In some cases, more sophisticated equipment such as high pressure liquid chromatography, gas chromatography, polarography, cyclic voltametry, mass spectrometry, or ultraviolet, visible, infra-red, or fluorescence spectrophotometry may be required to measure the reduced form of the electrochemically active substance.

In some cases, it may be desirable to react the reduced form of the electrochemically active substance so as to form a new compound which is more easily measured but whose concentration is proportional to the reduced form originally present.

EXAMPLES

The invention is illustrated by the following examples, without limitation to the scope of the invention.

Examples of Corrosion Detection by Electrochemically Active Compounds

Example 1

This test was run to screen some redox type indicators (group I) for detection of iron corrosion in water. The water was at room temperature and was allowed to equilibrate with the atmosphere so that the dissolved oxygen concentration was high. A mild steel coupon was placed in a beaker containing a 0.1 percent solution of each of the redox type indicators and a one percent solution of sodium chloride to accelerate the corrosion reaction. The color in the beaker was observed with time. The results are shown in Table 1.

TABLE 1

| Compound No. | Name | Initial | Final |
|---|---|---|---|
| 1 | Neutral Red | red | yellow |
| 2 | Resazurin | blue | red |

The results show that Compounds 1 and 2 had the proper potential to detect iron corrosion under the conditions of the test.

Example 2

This test was run to screen commercially available dinitrobenzene compounds (group II) for detection of corrosion on a variety of metals. The coupons were placed in a test tube containing a dilute solution of the test compound and two percent sodium chloride. The color of the solution was observed with time (all solutions were colorless initially). In addition, the percent decrease was measured for two of the compounds using liquid chromatography. The compounds tested are listed in Table 2. The visual results are given in Table 3, and the liquid chromatography results are given in Table 4.

TABLE 2

| Compound No. | Name |
|---|---|
| 1 | o-dinitrobenzene |
| 2 | p-dinitrobenzene |
| 3 | m-dinitrobenzene |
| 4 | 2,5-dinitrophenol |
| 5 | 3,4-dinitrobenzyl alcohol |
| 6 | 3,4-dinitrobenzoic acid |
| 7 | 3,5-dinitrobenzoic acid |

TABLE 3

| Compound No. | Color at End of Test | | | | |
|---|---|---|---|---|---|
| | a | b | c | d | e |
| 1 | colorless | colorless | purple | purple | purple |
| 2 | colorless | colorless | orange | orange | orange |
| 3 | colorless | colorless | colorless | colorless | colorless |
| 4 | colorless | colorless | orange | orange | orange |
| 5 | colorless | colorless | purple | purple | purple |
| 6 | colorless | colorless | purple | purple | purple |
| 7 | colorless | colorless | colorless | colorless | colorless |

Metal Coupons:
a. copper
b. admiralty brass
c. zinc
d. mild steel
e. aluminum

TABLE 4

| Compound No. | Coupon Type | Time (min) vs. Percent Reduction | | | | |
|---|---|---|---|---|---|---|
| | | 0 | 1 | 5 | 20 | 60 |
| 1 | a (copper) | 0 | 1 | 2 | 4 | 3 |
| 1 | d (mild steel) | 0 | 0 | 7 | 13 | 43 |
| 3 | a (copper) | 0 | — | 0 | 0 | 2 |
| 3 | d (mild steel) | 0 | — | 6 | 14 | 47 |

The results in Table 3 show that none of the compounds had the proper potential to show visible reduction for copper or admiralty brass. All of the compounds except #3 and #7 were visibly reduced by the rest of the metals. Since these two compounds have reduction potentials similar to the rest, liquid chromatography was run on #3 to see if the problem was that the reduced form was colorless.

The results in Table 4 show that the expected reduction was taking place for Compound No. 3 in the presence of mild steel to an extent similar to that being measured for Compound No. 1 in the presence of mild steel. Neither compound showed any significant reaction with copper.

Example 3

This test was run to screen some general organic compounds (group II) which are electrochemically active. The conditions of the test were the same as Example 12. The compounds tested and results are listed in Table 5.

TABLE 5

| Compound No. | Compound Name | Percent Reduction | | | | | |
|---|---|---|---|---|---|---|---|
| | | a | b | c | d | e | f |
| 1 | hydroquinone | 100 | 100 | 79 | 83 | 44 | 15 |
| 2 | benzoquinone | 100 | 100 | 100 | 100 | 67 | 0 |
| 3 | catechol | 41 | 59 | 33 | 54 | 18 | 10 |
| 4 | 3-cyanopyridine | 8 | 7 | 20 | 11 | 1 | 0 |

Metal Coupons:
a. copper
b. admiralty brass
c. zinc
d. mild steel
e. aluminum
f. blank

Example 4

This test was run to test commercially available tetrazolium compounds (group II) for detection of iron corrosion. The test conditions were the same as given in Example 1. The general structure for tetrazolium compounds is:

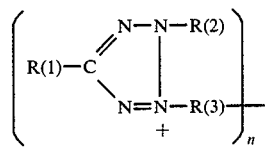

where $R_1$, $R_2$, and $R_3$ are from the group consisting of lower alkyl, aryl, aralkyl, heterocyclic substituted aryl with the proviso that neither $R_1$, $R_2$, and $R_3$ contain more than 14 carbon atoms and n may 1 or 2. At the proper potential, the tetrazolium ring is reduced to the formazan, whose general structure is:

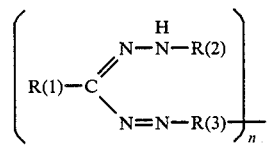

The compounds that were tested are listed in Table 6 and the results of the test are given in Table 7.

TABLE 6

| Compound No. | $R_1$ | $R_2$ | $R_3$ | n |
|---|---|---|---|---|
| 1 | $C_6H_5$ | p-$NO_2C_6H_4$ | o-$CH_3OC_6H_4$ | 2 |
| 2 | p-$NO_2C_6H_4$ | p-$NO_2C_6H_4$ | o-$CH_3OC_6H_4$ | 2 |
| 3 | $C_6H_5$ | p-$IC_6H_4$ | p-$NO_2C_6H_4$ | 1 |
| 4 | p-$H_2NSCC_6H_4$ | p-$NO_2C_6H_4$ | o-$CH_3OC_6H_4$ | 2 |
| 5 | $C_6H_5$ | $C_6H_5$ | 4,5-dimethyl-thiazol-2-yl | 1 |
| 6 | $C_6H_5$ | $C_6H_5$ | 1-naphthyl | 1 |
| 7 | $C_6H_5$ | $C_6H_5$ | o-$CH_3OC_6H_4$ | 2 |
| 8 | $C_6H_5$ | $C_6H_5$ | $C_6H_5$ | 2 |
| 9 | $C_6H_5$ | $C_6H_5$ | $C_6H_5$ | 1 |

TABLE 7

| Compound No. | Initial Color | Final Color | Time to Color |
|---|---|---|---|
| 1 | light yellow | blue | <3 min |
| 2 | light yellow | blue | <3 min |
| 3 | colorless | red | <3 min |
| 4 | light yellow | blue | 5 min |
| 5 | light yellow | blue | 7 min |
| 6 | colorless | purple | 12 min |

TABLE 7-continued

| Compound No. | Initial Color | Final Color | Time to Color |
|---|---|---|---|
| 7 | colorless | blue | 28 min |
| 8 | colorless | blue | 35 min |
| 9 | colorless | red | 80 min |

Note:
The final color for all samples as a precipitate on the metal surface.

All of the commercial tetrazolium compounds detect iron corrosion under the conditions of the test. Even though the reduction potential of the tetrazolium ring is very similar in all of the above compounds, it can be seen that the ring substituents had a definite effect on the kinetics.

Example of Preparation of Tetrazolium Salt

Because the reduced forms of the commercially available tetrazolium salts tested in Example 4 are insoluble, they would present a measurement problem when used in an actual corrosion detection test. The reduced form (the formazan) would precipitate at the corrosion site and be difficult to detect quantitatively in the water sample taken far from the corrosion site. Introduction of a functional group to give water solubility to the reduced form was done to eliminate this problem. Examples of such functional groups are carboxy (COOH), hydroxy (OH), sulfonic ($OSO_3H$), amino ($NH_2$), etc. These could be introduced on any of the three "R" groups in the generalized tetrazolium structure given below by choosing the appropriate organic compound to be used in the synthesis.

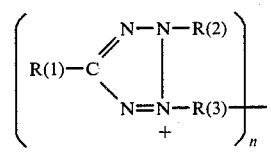

The reaction route leading to synthesis of tetrazolium compounds is well established in the literature. It generally involves reaction of an aldehyde with an aromatic hydrazine under basic conditions to form a phenyl hydrazone compound. The aldehyde may be aliphatic or aromatic. The phenyl hydrazone is then reacted with an aromatic diazonium salt to yield the formazan. This can generally be isolated by filtration after precipitation with water. The formazan is then oxidized either chemically (with bromine, isoamyl nitrite, lead tetra-acetate, etc.) or electrochemically to form the tetrazolium salt. The anion obtained depends upon the method of oxidation.

In this example benzaldehyde was reacted with p-hydrazinobenzoic acid to make the hydrazone, which was then reacted with diazotized aniline to make the formazan. Oxidation to the tetrazolium was accomplished with bromine in methanol.

Two sources were used for the p-hydrazinobenzoic acid. One source was 98% pure and the other, 97% pure. Benzaldehyde was purified prior to use by distillation under nitrogen from a small amount of zinc dust. Aniline was also purified prior to use by distillation from a small amount of zinc dust. The p-hydrazinobenzoic acid (0.1 moles) was added to benzaldehyde (0.1 moles) which had been dissolved in 180 ml of pyridine. The mixture was stirred overnight at room temperature to form the hydrazone. A dark brown solution resulted.

In a separate flask, aniline (0.1 moles) was dissolved in a mixture of glacial acetic acid (35 ml) and concentrated hydrochloric acid (30 ml). After cooling to <5 degrees C. with a salt-ice bath, sodium nitrite (0.11 moles) dissolved in water (15 ml) was added dropwise with stirring to form the diazonium compound. The temperature was maintained below 5 degrees C. at all times. The solution color was a light yellow.

The hydrazone solution was cooled <5 degrees C., and the diazonium salt solution was slowly added over a 30 minute period with stirring while again maintaining the 5 degrees C. temperature. Within minutes the solution turned from dark brown to dark purple as the formazan was formed. The ice bath was removed and the solution was stirred overnight at room temperature to complete the reaction.

The mixture was transferred to a one liter separatory funnel, and 500 ml of water was added. Immediately, a heavy, purple-red precipitate was formed which was collected by filtration through glass wool. Recrystallization several times from hot ethanol and vacuum drying at 40 degrees C. eventually yielded a dark purplish-black powder. The overall yield of the reaction was low (about 10%).

The formazan solid was dissolved in methanol. Oxidation to the tetrazolium bromide was accomplished by adding a concentrated solution of bromine in methanol dropwise with stirring until the color of the solution turned from deep purple to light orange. Evaporation of the methanol and vacuum drying at 40 degrees C. gave yellow-orange crystals of the synthesized tetrazolium bromide.

Example 5

The corrosion detection performance of the synthesized tetrazolium bromide was measured in a recirculation tank. The configuration of the system is shown in FIG. 1.

Water is recirculated around a metal pipe containing a heating element to provide the desired heat flux. Visual observation of the metal surface is possible through the plexiglass tube. A cold water recirculation coil in the basin cools the return water to maintain the selected basin temperature. An air purge in the basin maintains a saturated dissolved oxygen content.

14 ppm of tetrazolium compound was added to recirculating tap water. The heater and the cooling water was off. No makeup water or chemical treatment was added. The formazan generated by the corroding iron was extracted from 200 ml samples of the water and measured quantitavely by liquid chromatography. Table 8 gives the formazan concentrations and describes the physical appearance of the pipe vs. time.

TABLE 8

| Sample No. | Time (hrs) | Formazan (ppb) | Appearance of pipe |
|---|---|---|---|
| 1 | 0 | <1 | clean surface |
| 2 | 0.1 | 2 | clean surface |
| 3 | 0.5 | 2 | beginning of flash corrosion |
| 4 | 1.0 | 1 | 5% flash corrosion |
| 5 | 1.5 | 1 | 10% flash corrosion |
| 6 | 2.0 | 2 | 20% flass corrosion, beginning rust |
| 7 | 3.0 | 19 | 30% rust |
| 8 | 4.0 | 180 | 40% rust |
| 9 | 5.0 | 400 | 50% rust |
| 10 | 6.0 | 760 | >50% rust |

As can be seen, the levels of formazan generated increased as corrosion progressed. This test demonstrated that the tetrazolium compound would react with cathodic sites on a corroding iron surface to form a water soluble formazan. It also showed that extraction and analysis of the formazan was feasible and that the amount measured corresponded to the amount of corrosion that had occurred.

Example 6

This test was run to determine the ability of the tetrazolium compound to measure corrosion on some other metal surfaces. Copper would not be expected to be detected since its open circuit potential in aqueous solution of moderate conductivity would be predicted to be more positive than the tetrazolium reduction potential. Admiralty brass is mostly copper but contains some zinc in elemental form which has a more negative potential than tetrazolium. Admiralty brass also has a more negative potential than tetrazolium. Hence, corrosion should be detectable by tetrazolium in admiralty brass. Aluminum has a very negative potential and thus aluminum corrosion should be easily detected.

The recirculation system was as given in Example 5 above. High conductivity water (4000 micromhos) was used to promote corrosion. The heater was turned off. No corrosion inhibitor product was added to the tests initially. The tetrazolium compound was added at a level of 1.0 ppm. The results are shown in Table 9.

TABLE 9

| Sample No. | Day No. | Formazan (ppb) copper | admiralty brass | aluminum |
|---|---|---|---|---|
| 1 | 1 | 0.03 | 0.20 | 0.98 |
| 2 | 2 | 0.05 | 0.32 | 8.1 |
| 3 | 3 | 0.04 | 0.13 | 6.0 |
| 4 | 4 | — | 0.05 | 5.0 |

As expected, no formazan generation was seen on the copper tube and very high levels of formazan were seen on the aluminum tube. Moderate levels of formazan were seen on the admiralty brass tube corresponding to the expected de-zincification reaction. After day 2, a nitrite-molybdate corrosion inhibitor was added to the brass and aluminum systems. In both cases, corrosion rates decreased at longer times.

Example 7

This test attempted to reproduce typical cooling water conditions. Formazan levels were measured by extraction and liquid chromatography as before. In addition, the total iron level was monitored by atomic absorption beginning on day 5.

The recirculation tank was as given in Example 5 above. The system was initially charged with equal volumes of make-up waters "A" and "B" to give the equivalent of four cycle tap water. Make-up waters "A" and "B" were then slowly added at a 1:1 ratio during the test to provide turnover of the system and to compensate for any evaporative losses. Their composition is given in Table 10.

TABLE 10

| | grams/l | ppm as $CaCO_3$ |
|---|---|---|
| Make-Up Water "A": | | |
| Sodium Bicarbonate | 1.48 | 880 |
| Make-Up Water "B": | | |
| Calcium Chloride dihydrate | 1.06 | 720 |
| Magnesium Sulfate heptahydrate | 0.99 | 400 |

Blowdown was adjusted to maintain four cycles of concentration and give a system turnover time of 29 hours. Treatment chemicals were fed through syringe pumps. Inhibitor A[1] was fed to maintain 100 ppm in the system. Heat flux was 12,500 Btu/square foot/hr. Basin temperature was 120 degrees F. (49 degrees C.). The pH was controlled automatically using a feed of either 2% sulfuric acid or 2% sodium hydroxide.

[1]"Inhibitor A"=a commercial inhibitor containing as its active ingredients a low molecular weight acrylic acid polymer, organic phosphonates, and toluene triazole.

Initially, a 10 ppm spike of tetrazolium compound was added within 30 minutes of start-up before passivation had occurred. Formazan was quickly generated that corresponded to the orange flash corrosion being observed on the pipe surface. By the end of the first day, the surface was passivated, the orange hematite/iron hydroxide mix changing to black magnetite, and the formazan level had peaked at 23 ppb. The level decayed over the next three days due to blowdown and passivation of the system.

At day 4, a continuous 4 ppm tetrazolium feed was begun. After an initial slight surge in formazan generation, the system stabilized at 2–3 ppb, corresponding to the steady state 1–2 mils per year (mpy) corrosion rate expected with an Inhibitor A program. The appearance of the pipe was still the same, consisting of a few widely scattered black streaks and spots. The iron level was a steady 0.05 ppm.

At day 11, an acid upset was simulated by slowly adding dilute (2%) sulfuric acid until the pH had dropped from 9.0 to 8.0 and the alkalinity had dropped from 440 ppm to 40 ppm. The visual initiation of red-brown corrosion was paralleled by the corresponding formazan level increase to 7 ppb (sample #20) and iron level increase to 0.4 ppm, and then 0.7 ppm. At the end of 22 hours, heavy brown rust was apparent on the surface of the pipe, the formazan level was up to 36 ppb (sample #22), and the iron concentration had increased to 7.0 ppm. The recirculating water contained red iron floc.

At this point sodium bicarbonate was added to bring the pH back up to 9.0 and increase the alkalinity back up to 440 ppm simulating correction of the acid-upset condition. By the end of the day, the formazan level had dropped to 8 ppb, indicating repassivation. The iron level from recirculating iron floc and dissolved iron continued to hold at 7 ppm. The pipe was coated with a heavy tubercular layer of red-brown rust.

During the next three days, the system maintained a low corrosion rate, generating 5 ppb formazan on day #14 and 4 ppb on day #15. The iron measurements continued to show about 7 ppm. The system was running without pH control.

At the end of day #15, the alkalinity apparently dropped low enough to again lose corrosion protection. The formazan and iron levels began to increase again, reaching 39 ppb and 25 ppm, respectively, on day #17.

At this point, the tetrazolium compound feed was stopped. The decay curve of the formazan can be seen over the next few days due to system blowdown.

This test demonstrated the use of the tetrazolium compound as a practical method of monitoring corrosion. Low corrosion rates were successfully monitored, as shown by the 1–2 mpy rates typical of Inhibitor A that were seen during days 8–11.

Only active corrosion was measured, as shown by the low formazan levels measured after repassivation on day 12 despite the heavy corrosion deposits on the metal surface. In addition, under-deposit corrosion was detected, as can be seen by the high levels of formazan detected during the upset commencing on day 15 well after heavy tubercular deposits had been formed on the surface.

Example 8

Figure 2:
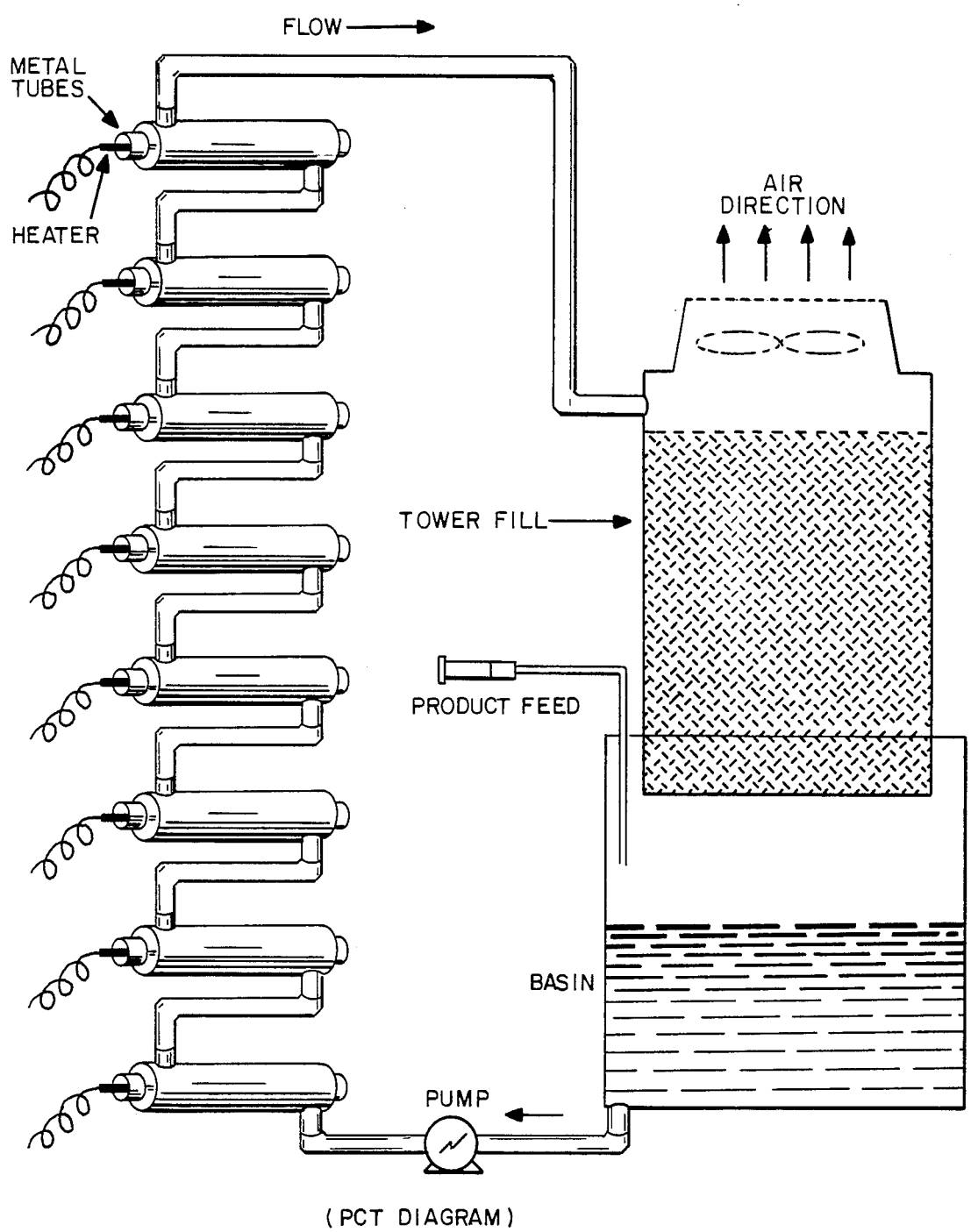
FIG. 2 is another diagramatic view of a pilot cooling tower apparatus.

This test was run on a larger scale than Examples 5 and 7 to verify the performance of the tetrazolium compound as a corrosion detection compound. A pilot cooling tower (PCT) was used to simulate a large scale cooling water system. Its configuration is given in FIG. 2.

The system was charged with tap water, then allowed to cycle up to six cycles. The basin temperature was 100° F. All tubes were mild steel. Inhibitor A was fed at startup at a level of 200 ppm to inhibit corrosion while the tubes were scaling up. The results are shown in Table 11.

TABLE 11

| Sample # | Day # | ppm Inhibitor | ppm Formazan | ppm Fe | ppm M Alk |
|---|---|---|---|---|---|
| 1 | 1 | — | — | — | — |
| 2 | 2 | 167 | 0.17 | 0.69 | 330 |
| 3 | 3 | 129 | 0.11 | 0.43 | 520 |
| 4 | 6 | 17 | 0.49 | 0.06 | 318 |
| 5 | 7 | 11 | 0.06 | — | 284 |
| 6 | 8 | 14 | 0.06 | 0.10 | 308 |
| 7 | 13 | 41 | 0.06 | 0.08 | 416 |
| 8 | 14 | 5 | 0.10 | 0.04 | 302 |
| 9 | 15 | 41 | 0.06 | 0.10 | 370 |
| 10 | 16 | 20 | 0.11 | 0.06 | 330 |
| 11 | 17 | 23 | 0.34 | 0.05 | 330 |
| 12 | 20 | 22 | 0.15 | 0.08 | 328 |
| 13 | 21 | 190 | 0.10 | 0.14 | 432 |
| 14 | 22 | 163 | 0.04 | — | 532 |
| 15 | 22 | — | 0.03 | — | — |
| 16 | 23 | 140 | 0.03 | 0.13 | 492 |
| 17 | 23 | — | 0.21 | — | — |
| 18 | 24 | 133 | 0.04 | <0.05 | 412 |
| 19 | 27 | 86 | 0.03 | 0.06 | 382 |
| 20 | 27 | — | 0.07 | — | — |
| 21 | 28 | 124 | 0.03 | 0.09 | 132 |
| 22 | 29 | 121 | 0.02 | 0.06 | 254 |
| 23 | 30 | 167 | 0.14 | 0.70 | 10 |
| 24 | 31 | 134 | 0.06 | 1.13 | 150 |

The tetrazolium compound detected the corrosion developed during days 1–4. An even scale did not form on the tube surfaces. During days 16–20, a rise in formazan concentration occurred which evidently corresponded to active corrosion due to low Inhibitor A level. Addition of Inhibitor A immediately ended the corrosion (day 21). On days 23 and 29, sulfuric acid was added to simulate upsets which would be expected to cause corrosion. Each time an increase in formazan level was seen to occur (0.21 ppb and 0.14 ppb, respectively).

Example 9

This test was run on a larger scale than Example 6 to verify the performance of the tetrazolium compound with a nitrite-molybdate corrosion inhibitor on mild steel, copper, and aluminum tubes. The configuration of the pilot cooling tower (PCT) was as given in FIG. 2. The system was charged with low hardness water containing 300 ppm inhibitor. There were four mild steel tubes containing no heat load and four copper tubes that were heated. The tetrazolium compound was fed at 0.1 ppm. The results are given in Table 12 below.

TABLE 12

| Sample No. | Day No. | Formazan (ppb) |
|---|---|---|
| 1 | 0 | 0.45 |
| 2 | 1 | <0.05 |
| 3 | 3 | <0.05 |
| 4 | 4 | <0.05 |
| 5 | 5 | <0.05 |
| 6 | 6 | <0.05 |
| 7 | 7 | <0.05 |
| 8 | 10 | 0.05 |
| 9 | 10 | <0.05 |
| 10 | 11 | <0.05 |
| 11 | 13* | <0.05 |
| 12 | 14 | 0.09 |
| 13 | 17 | 0.18 |
| 14 | 18 | 0.08 |
| 15 | 19 | 0.06 |
| 16 | 20 | 0.09 |
| 17 | 21 | 0.08 |

After the initial flash corrosion (Sample #1) corrosion slowed and low formazan levels were measured. However, the levels were lower than that expected based on the appearance of the tubes which were showing moderate corrosion. At Sample No. 11 (asterisk) the tetrazolium feed was increased to give 1.0 ppm. Detectable formazan levels were immediately measured.

Example 10

This test was run to determine the effect of replacing the copper heated tubes with aluminum heated tubes. All other conditions were exactly the same as Example 9 above. The tetrazolium compound was fed at 1.0 ppm. The results are given in Table 13 below.

TABLE 13

| Sample No. | Day No. | Formazan (ppb) |
|---|---|---|
| 1 | 1 | 21 |
| 2 | 4 | 2.1 |
| 3 | 5 | 0.88 |
| 4 | 6 | 0.67 |

The formazan levels were very high, but the appearances of the mild steel tubes were the same as in Example 9 above. This indicated that aluminum corrosion was being detected and was slowly decreasing.

Having thus described my invention, I claim:

1. A method for determining the corrosion rate of metals in contact with a liquid system which is capable of causing corrosion of such metals which comprises adding to the liquid system a soluble electrochemically active compound having a reduction potential more positive than the metal in contact with the liquid system and then monitoring the system thus treated with the electrochemically active compound by analytically detecting the soluble reduced form of the electrochemically active compound which was produced in situ and correlating the amount of the reduced form with the amount of corrosion.

2. The method of claim 1 wherein the liquid system is a non-aqueous system.

3. A method for determining the corrosion rate of ferrous metals in contact with an aqueous system capable of causing the corrosion of such ferrous metals which comprises adding to the aqueous system a soluble electrochemically active tetrazolium compound having a reduction potential more positive than the ferrous metals in contact with the aqueous system and then monitoring the system thus treated by analytically detecting the soluble reduced form, which was produced in situ, of the electrochemically active tetrazolium compound and correlating the amount of the reduced form with the amount of corrosion.

* * * * *